United States Patent
Skog et al.

(10) Patent No.: US 11,457,899 B2
(45) Date of Patent: Oct. 4, 2022

(54) APPARATUSES, METHODS, AND SYSTEMS FOR SAMPLE COLLECTION AND DISPERSION

(71) Applicant: EXOSOME DIAGNOSTICS, INC., Cambridge, MA (US)

(72) Inventors: Johan Skog, Charlestown, MA (US); Bill Tisel, Chaska, MN (US); Joseph Baker, Fallbrook, CA (US)

(73) Assignee: Exosome Diagnostics, Inc., Waltham, MA (US)

( * ) Notice: Subject to any disclaimer, the term of this patent is extended or adjusted under 35 U.S.C. 154(b) by 823 days.

(21) Appl. No.: 15/515,980

(22) PCT Filed: Sep. 30, 2015

(86) PCT No.: PCT/US2015/053296
§ 371 (c)(1),
(2) Date: Mar. 30, 2017

(87) PCT Pub. No.: WO2016/054252
PCT Pub. Date: Apr. 7, 2016

(65) Prior Publication Data
US 2017/0296155 A1    Oct. 19, 2017

Related U.S. Application Data

(60) Provisional application No. 62/057,575, filed on Sep. 30, 2014.

(51) Int. Cl.
*A61B 10/00*   (2006.01)
*A61B 90/90*   (2016.01)
*B01L 3/00*    (2006.01)

(52) U.S. Cl.
CPC ............ *A61B 10/007* (2013.01); *A61B 90/90* (2016.02); *B01L 3/50825* (2013.01);
(Continued)

(58) Field of Classification Search
None
See application file for complete search history.

(56) References Cited

U.S. PATENT DOCUMENTS 3,536,061 A * 10/1970 Ogle ................. A61B 5/150389
                                                           600/577
3,722,503 A *  3/1973 Hovick .................... A61F 5/44
                                                           600/574
(Continued)

FOREIGN PATENT DOCUMENTS

CA    2181305 A1    1/1998
DE    41 32 480 A1  4/1993
(Continued)

OTHER PUBLICATIONS

Extended European Search Report for European Application No. 15847932.9, dated May 11, 2018, 4 pages.
(Continued)

*Primary Examiner* — Allen Porter
*Assistant Examiner* — Samuel C Kim
(74) *Attorney, Agent, or Firm* — Cooley LLP; Matthew Pavao; Brian P. Hopkins

(57) ABSTRACT

In order to address an inability to separate portions of a sample and/or substance, in some embodiments, methods and apparatuses for separating components and/or portions of a sample are provided. For example, a sample collection container may comprise two areas within the container, one which is configured to contain a first volume of the sample, and one which is configured to contain a second volume of the sample. A float device may be configured to seal the portion of the container collecting the first volume from the portion of the container collecting the second volume, after the former portion of the container has been filled. The sample collection container may further comprise a top cap
(Continued)

configured to further seal the two portions of the container, and to prevent leakage and/or spilling of the sample from the sample collection container.

4 Claims, 20 Drawing Sheets

(52) U.S. Cl.
CPC . *B01L 2200/0689* (2013.01); *B01L 2200/087* (2013.01); *B01L 2200/14* (2013.01); *B01L 2200/141* (2013.01); *B01L 2300/021* (2013.01); *B01L 2300/042* (2013.01); *B01L 2300/087* (2013.01); *B01L 2300/0832* (2013.01); *B01L 2300/0851* (2013.01)

(56) References Cited

U.S. PATENT DOCUMENTS

| | | | |
|---|---|---|---|
| 4,961,432 A | 10/1990 | Guirguis | |
| 5,454,958 A | 10/1995 | Fiehler | |
| 5,518,003 A * | 5/1996 | Allan | A61B 10/007 600/573 |
| 8,747,669 B1 | 6/2014 | Bonner et al. | |
| 2003/0021727 A1 | 1/2003 | Weyker et al. | |
| 2004/0209349 A1* | 10/2004 | Goldman | B01L 3/502 435/287.1 |
| 2004/0267159 A1 | 12/2004 | Yong et al. | |
| 2005/0059163 A1* | 3/2005 | Dastane | A61B 5/417 436/177 |
| 2010/0137743 A1* | 6/2010 | Nishtala | A61B 5/14507 600/575 |
| 2010/0140182 A1 | 6/2010 | Chapman et al. | |
| 2011/0237977 A1* | 9/2011 | Knight | A61B 10/007 600/573 |
| 2014/0213934 A1 | 7/2014 | Ellis et al. | |
| 2017/0296155 A1 | 10/2017 | Skog et al. | |

FOREIGN PATENT DOCUMENTS

| | | |
|---|---|---|
| DE | 10 2010 000 645 A1 | 9/2011 |
| WO | WO 2005/014173 A1 | 2/2005 |
| WO | WO 2007/149379 A2 | 12/2007 |
| WO | WO 2009/117212 A1 | 9/2009 |
| WO | WO 2010/036895 A1 | 4/2010 |
| WO | WO 2016/054252 A1 | 4/2016 |

OTHER PUBLICATIONS

International Preliminary Reporton Patentability for International Application No. PCT/US2015/053296, dated Apr. 4, 2017, 6 pages.
International Search Report and Written for International Application No. PCT/US2015/053296, dated Dec. 29, 2015, 8 pages.

* cited by examiner

704

702

706

802

804

806

808

1202

1204

1206

1302

1304

1802

1804

1806

1902

1904

APPARATUSES, METHODS, AND SYSTEMS FOR SAMPLE COLLECTION AND DISPERSION

CROSS-REFERENCES TO RELATED APPLICATIONS

This application is a National Phase of PCT Patent Application No. PCT/US2015/053296 having International filing date of Sep. 30, 2015, which claims benefit of and priority to U.S. Provisional Patent Application No. 62/057,575, entitled, "Apparatuses, Methods, and Systems for Sample Collection and Dispersion", filed Sep. 30, 2014, the disclosures of which are herein incorporated by reference in their entireties.

BACKGROUND

Conventional sample collection containers often collect samples in a single compartment of the container, and do not allow for separation of parts of the sample (e.g., to separate a first volume of the sample from the rest of the sample, to separate components of the sample, and/or the like). However, the first 20-40 mL and/or like quantity of a sample may contain the largest quantity of components of interest in the sample (e.g., for a urine sample, the first 25 mL of urine may contain the greatest concentration of hormones, exosomal RNA prostate cancer markers, and/or the like). Thus, such container designs can dilute the sample and make it difficult for laboratories to test the samples for abnormalities. Merely reducing the size of the container to 25 mL may be both cumbersome to a patient who must supply the sample, and may waste portions of the sample which could be used to test other ailments, e.g., the 26-40 mL of a urine sample left after the first volume of the sample may still be optimal for assessment of other illnesses such as bladder cancer and/or other disorders, even if it is not optimal for testing other ailments. Additionally, conventional sample collection containers often need to be shipped long distances in order to be analyzed at a laboratory, and can leak or spill, causing part of the sample to be lost in transit.

SUMMARY OF SOME OF THE EMBODIMENTS

In some embodiments, a biological sample (e.g., a urine sample, and/or the like) may be collected for analysis, e.g., to determine a person's health and/or the like. In some embodiments, a sample collection cup may be configured to separate portions of a sample from other portions of the sample (e.g., a first volume of the sample, and/or the like may be separated from other portions of the sample), in order to obtain optimal results. In some embodiments, parts of the container may be sealed in a plurality of ways in order to prevent leakage or spills, e.g., during transit and/or the like, and to prevent dilution of the portions of the sample.

In some embodiments, a plurality of designs may be utilized in order to easily collect and separate portions of a sample for optimal extraction, including a two-cup container, a bottom-cap container, and/or the like, using a float to separate a first volume of fluid from the second volume of fluid.

DETAILED DESCRIPTION OF SOME OF THE EMBODIMENTS

Figure 1:
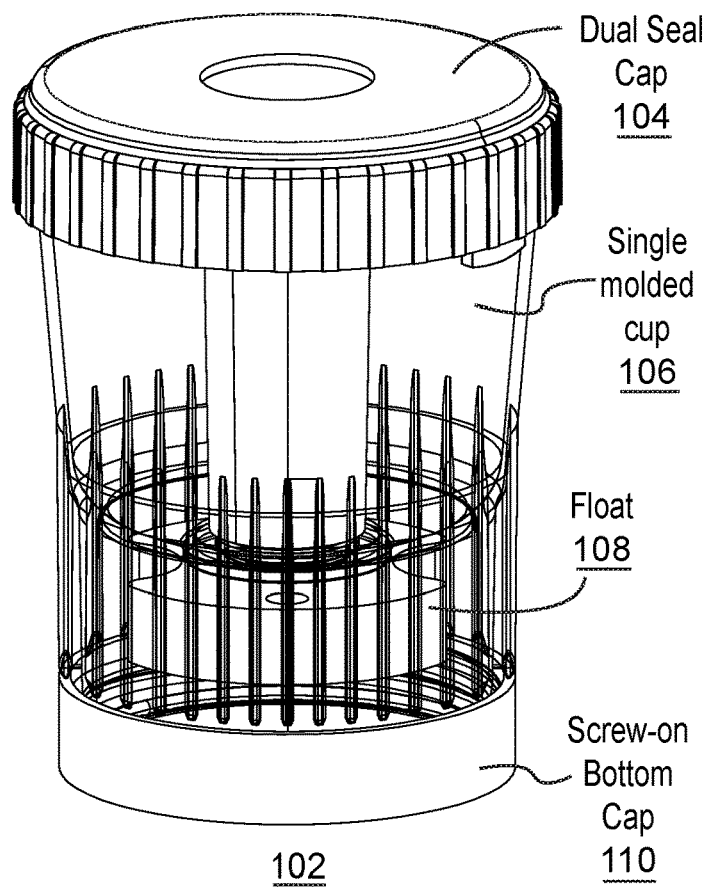
FIG. 1 shows a bottom-cap design for a sample collection container, according to some embodiments.
Figure 1:
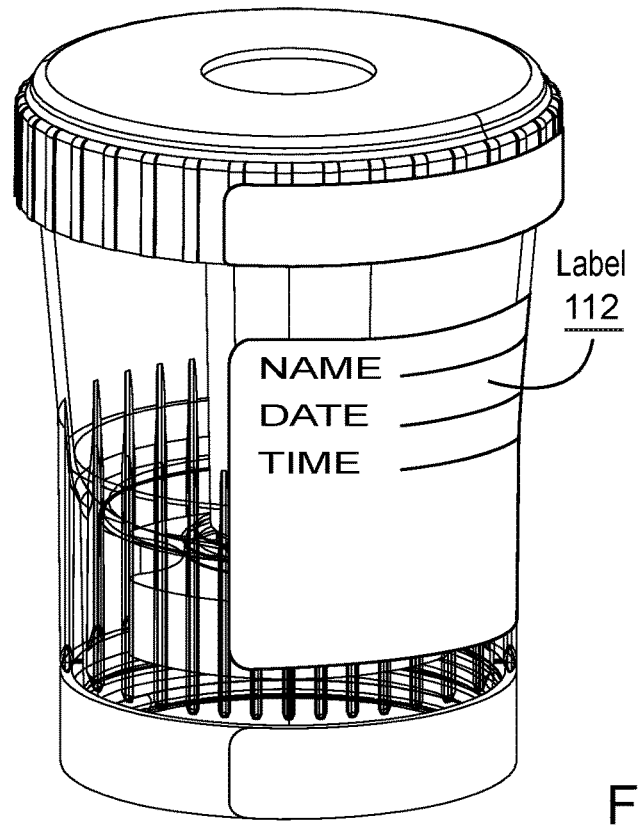
Figure 2:
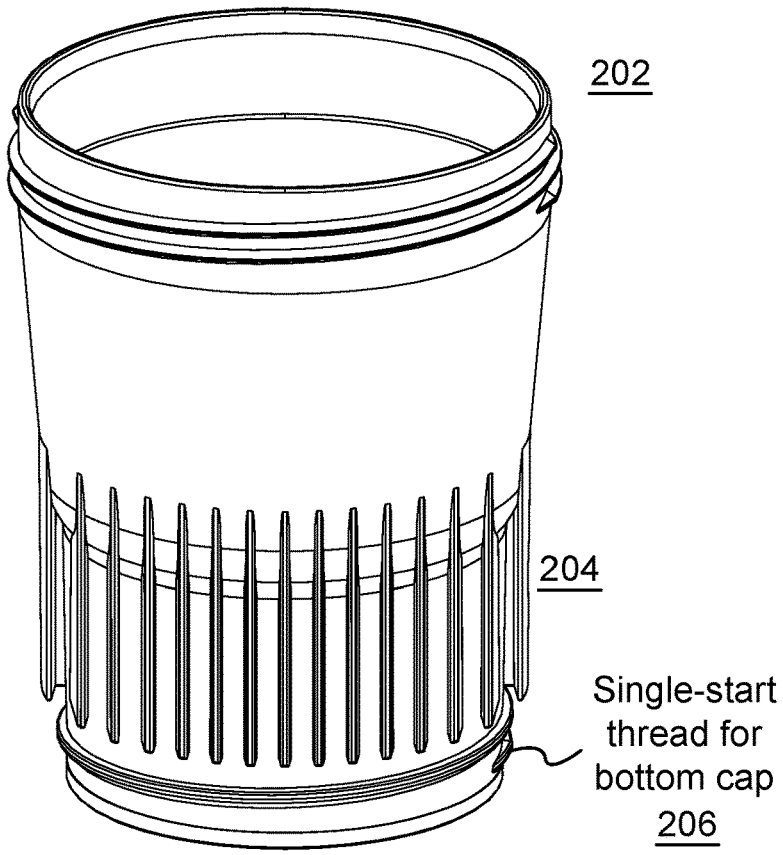
FIG. 2 shows a bottom-cap design for a sample collection container, according to some embodiments.
Figure 2:
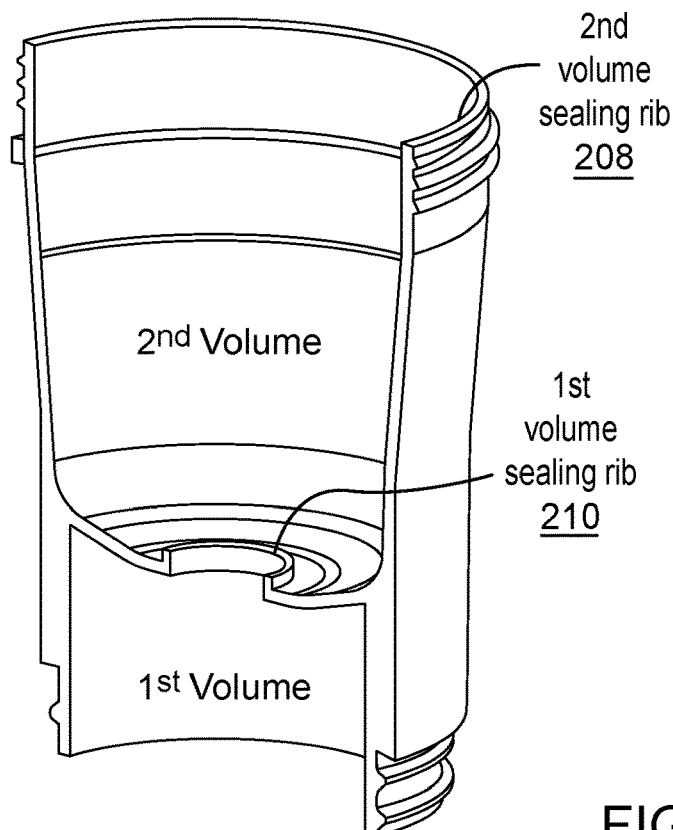
Figure 3:
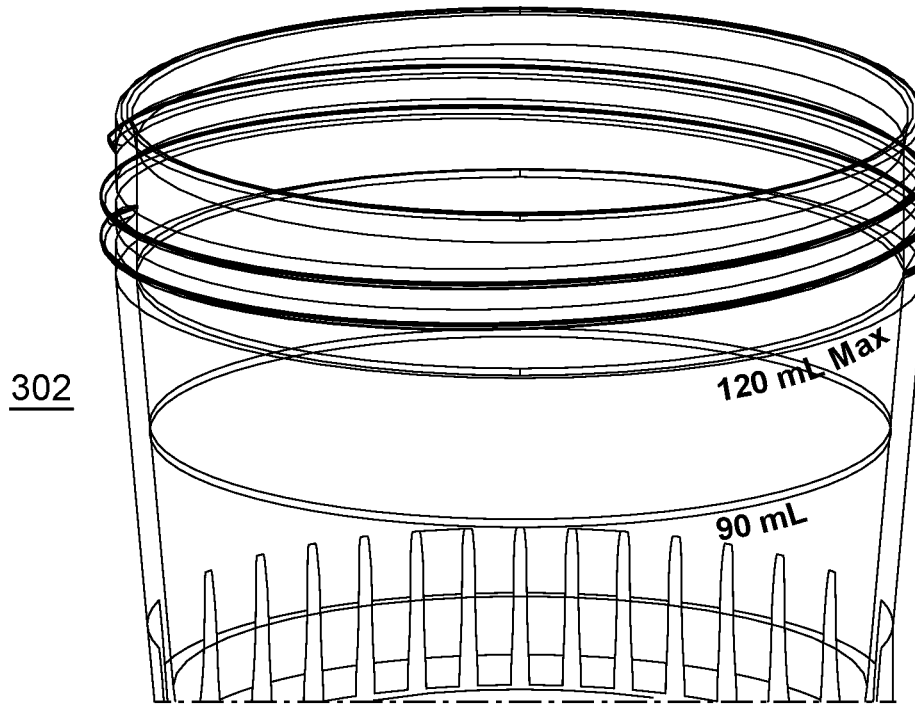
FIG. 3 shows volume markings for a sample collection container, according to some embodiments.
Figure 3:
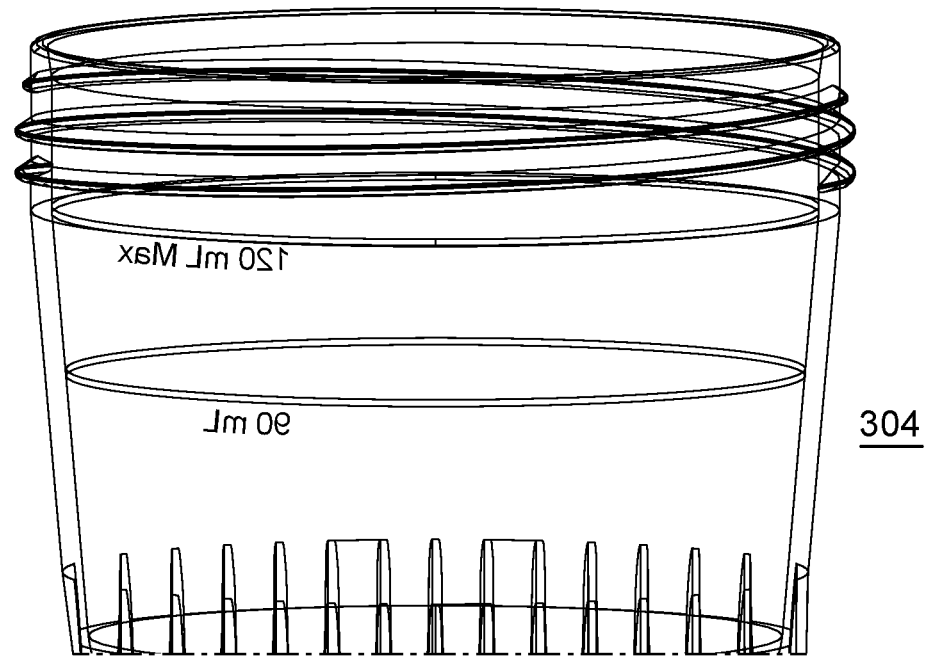

In some embodiments, sample collection containers may be formed via a bottom-cap design, a two-cup design, and/or the like. Referring to FIG. 1, in some embodiments, a laboratory may use a bottom-cap design 102 for the sample collection container. In some embodiments, the container may comprise a dual-seal top cap 104, a single molded collection cup 106, a float device 108, and a screw-on bottom cap 110. In some embodiments, the collection container may also have room for a label 112 on which sample identification information (e.g., the name of the patient, the date and time the sample was obtained, the type of sample obtained, and/or the like) may be imprinted. In some embodiments, referring to FIG. 2, an exemplary sample collection container may include a dual-start thread at the top of the container 202, e.g., for easy removal and placement of the top lid by a patient. The bottom cap 206 may be placed on the sample collection container on a single-start thread. The container may further comprise ribs on the sides of the container 204, e.g., to help a patient grip the container. Each section of the container may have a sealing rib 208, which may help seal the portion of the container and prevent spills (e.g., sealing rib 208 may prevent the sample from spilling out of the top lid, and sealing rib 210 may prevent the sample in the second volume from contaminating the sample collected in the first volume, and/or the like). Referring to FIG. 3, in some embodiments, the container may also comprise volumetric markings 302 and company logos 304, and/or like information.

Figure 4:
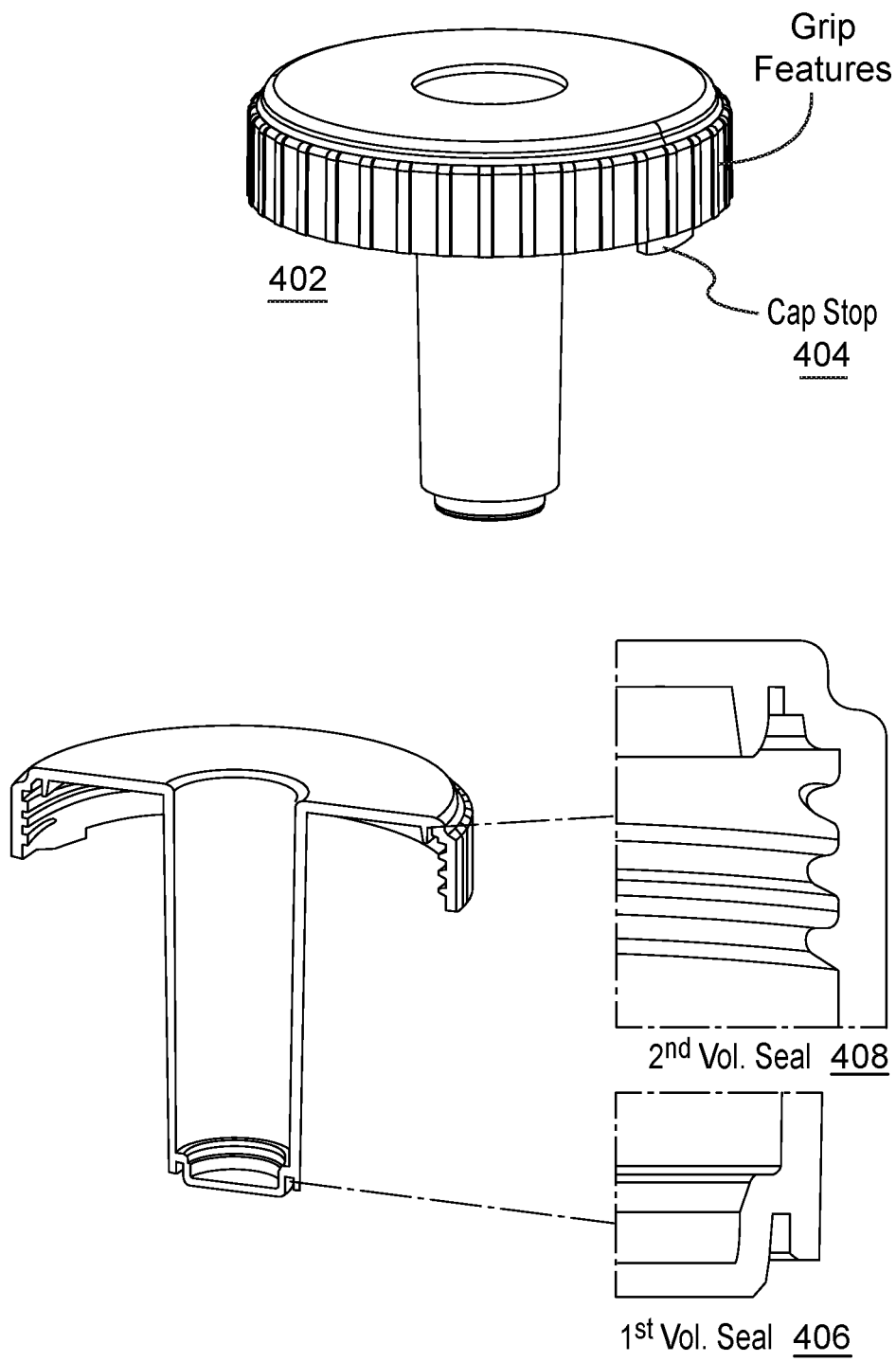
FIG. 4 shows a top cap for a sample collection container, according to some embodiments.

FIG. 4 shows a top cap for a sample collection container, according to some embodiments. For example, in some embodiments, a top cap 402 may comprise a screw cap with grip ridges, and a cap stop 404, e.g., to secure the cap and prevent the cap from turning too much in a particular direction. The cap may further comprise a long protrusion from the screw cap component, which may connect with the opening of the first volume of the container, and/or the like. In some embodiments, the cap may comprise at least two seals. For example, the cap may comprise a first volume seal 406 which may seal the opening of the first seal via connecting with sealing rib 210 in order to prevent leaking between the first and second volumes. The cap may further comprise a second volume seal 408 between the cap and the top of the container. In some embodiments, the second volume seal and the cap may comprise round threads.

Figure 5:
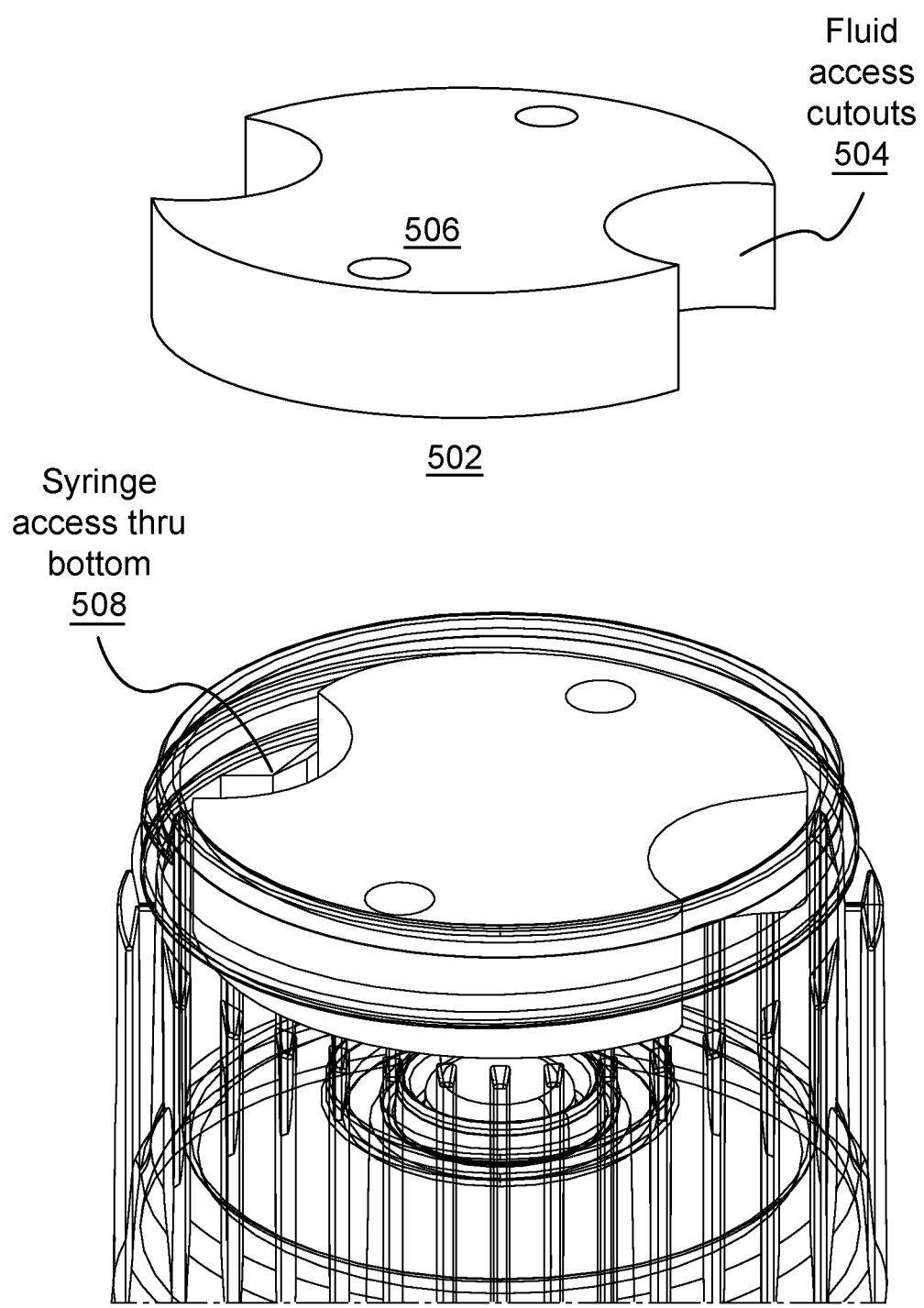
FIG. 5 shows a float design for a sample collection container, according to some embodiments.
Figure 6:
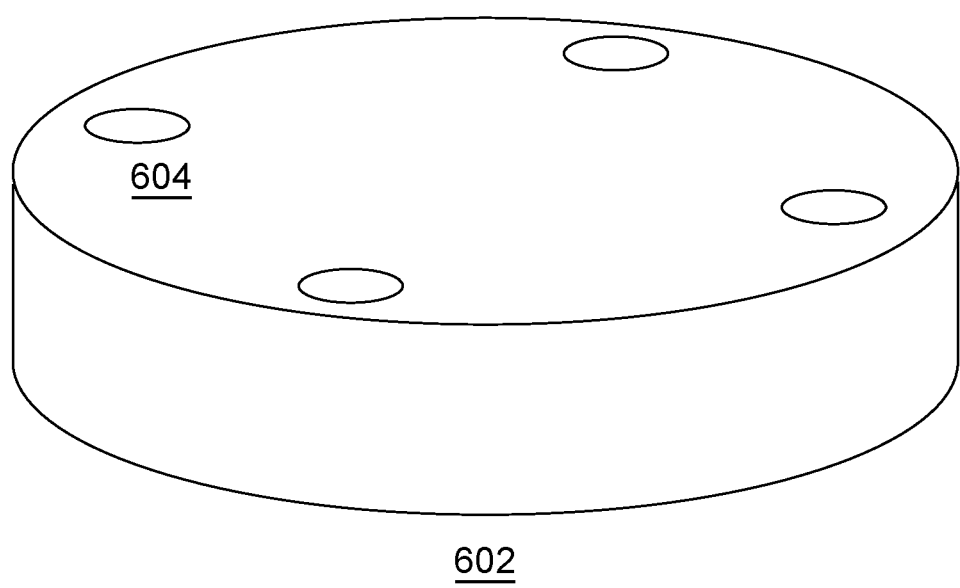
FIG. 6 shows a float design for a sample collection container, according to some embodiments.

FIGS. 5 and 6 show float designs for a sample collection container, according to some embodiments. In some embodiments, a float 502 may be a device and/or mechanism for preventing fluid flow between a first and second volume of the collection container when the first volume has filled, and may allow for extraction of the sample from the bottom cap with minimized contamination of the sample. In some embodiments the float may also prevent fluid from flowing into the first volume after the first volume has been filled. For example, in some embodiments, a float may comprise food grade PE foam with a density of 2.0 lb/cu. ft, and may have a thickness of 0.375 inches. In some embodiments, a float may have fluid pass-through holes 506 through which the sample may flow through until the first volume area has been filled, and/or fluid access cutouts 504 that laboratories may use to extract sample from the first volume (e.g., via a syringe and/or the like). The access cutouts and holes may be spaced such that the channel between the first and second volumes connects with the solid portion of the float when the container is filled, and such that the cutouts and holes cannot be aligned with the channel and allow sample in the second volume to contaminate the sample in the second volume. In some embodiments, a float 602 may not comprise any fluid access cutouts, and may instead comprise only pass-through holes 604, and/or the like. In some embodiments, after the top cap has sealed the first volume from the second volume, the container may be inverted, allowing the float to float towards the bottom cap of the container 508. Thus by inverting the container, a laboratory device and/or the like may be able to extract sample from the first volume via the holes and/or cutouts in the float.

Figure 7:
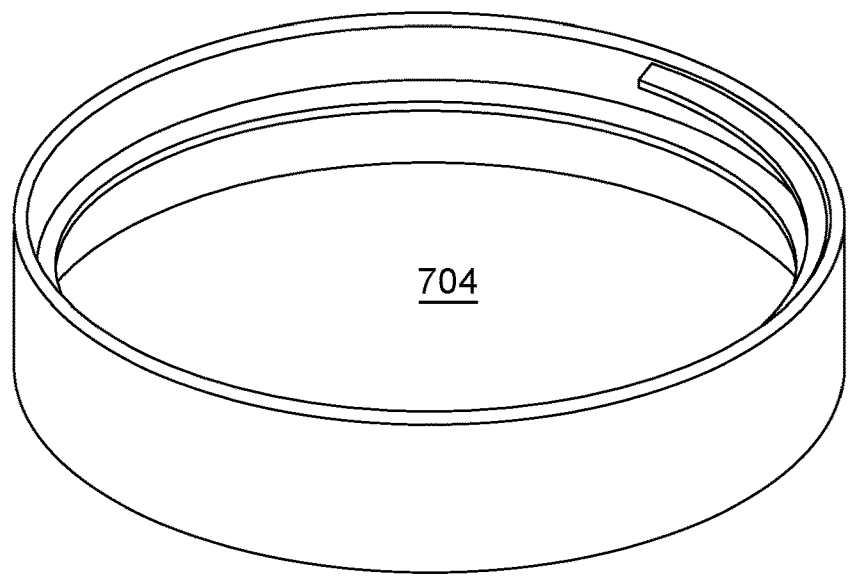
FIG. 7 shows a bottom cap design for a sample collection container, according to some embodiments.
Figure 7:
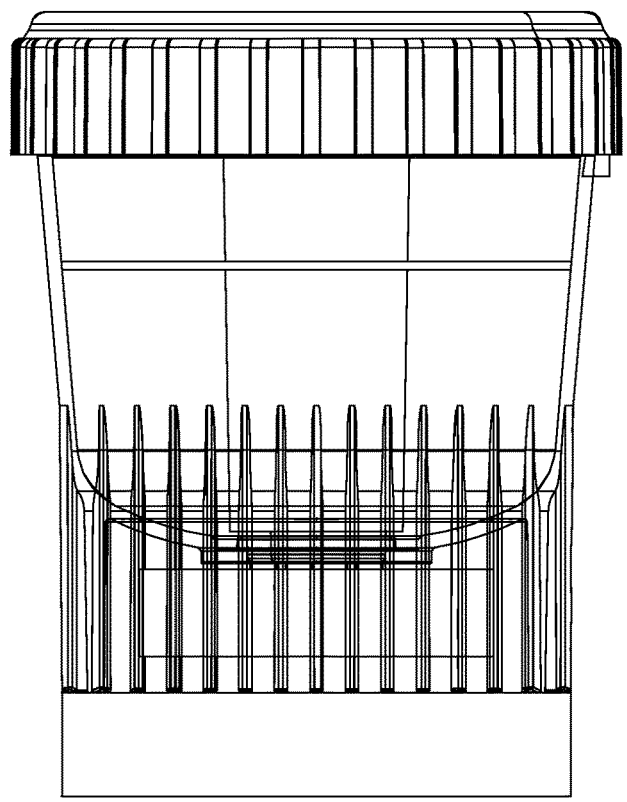

FIG. 7 shows a bottom cap design for a sample collection container, according to some embodiments. In some embodiments, the bottom cap 702 may have a 53-400 cap and single thread specification, and may be made out of polypropylene. The cap may comprise a core liner 704 comprising a layer of LDPE film, a layer of PE foam, and a layer of LDPE film, and/or a like composition). The bottom cap may sit flush to the rub bottoms on the container 706, and may maintain the outer diameter of the ribs. The seal on the bottom cap may create a container seal by compressing a flexible polyethylene membrane on the inside of the cap, and/or a similar mechanism.

Figure 8:
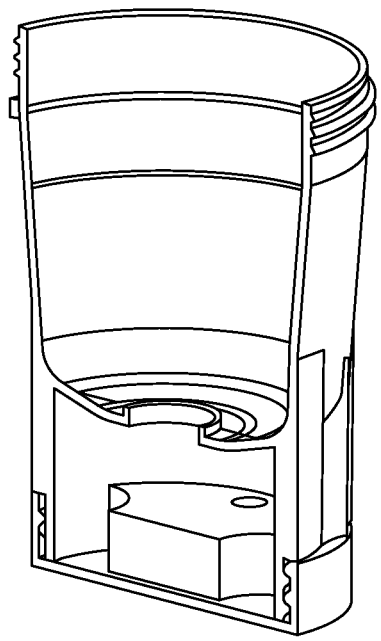
FIG. 8 shows filling a sample collection container, according to some embodiments.
Figure 8:
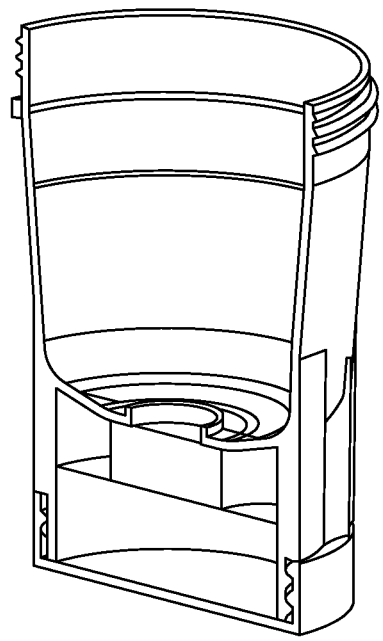
Figure 8:
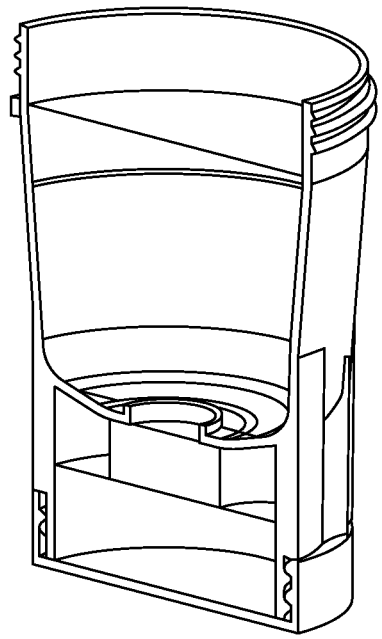
Figure 8:
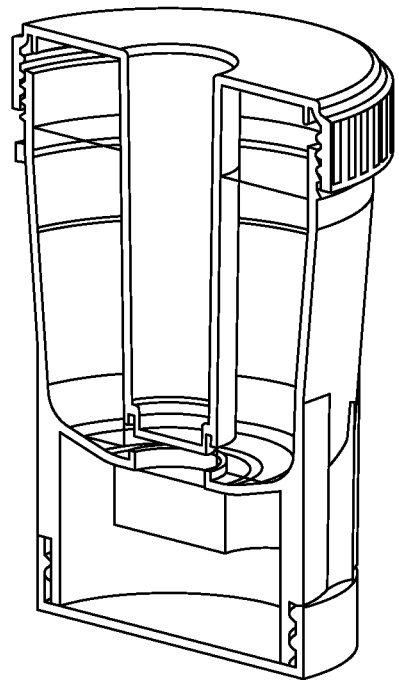

FIG. 8 shows filling a sample collection container, according to some embodiments. In some embodiments, a patient may be able to start filling the cup with their sample (e.g., a urine sample), which may first collect in a dead volume area above the first volume chamber (e.g., the lower volume chamber) 802. In some embodiments, the dead volume area may be able to hold 0.8 mL of sample, and/or the like. In some embodiments, there may not be a dead volume area, and the sample may immediately start to collect in the lower volume chamber. As the lower chamber fills with sample 804, the float may be able to rise, eventually being able to close off the lower chamber from the upper chamber. In some embodiments the lower volume chamber may be able to hold a volume (e.g., 20-25 mL, and/or any volume from, for example, 5 mL-40 mL, and/or the like) of sample, and/or a like amount. After the lower chamber has been filled, the upper chamber may still be filled 806; in some embodiments, the upper chamber may be able to hold 95 mL of sample, and/or a like amount. After the sample cup has been filled (e.g., at the top volumetric line on the container, and/or the like), the top cap may be placed on the container 808. The top cap may displace some volume of the sample as it closes (e.g., the cap may displace approximately 15 mL of the sample, causing the fluid in the container to raise 0.17 inches, and/or the like).

Figure 9:
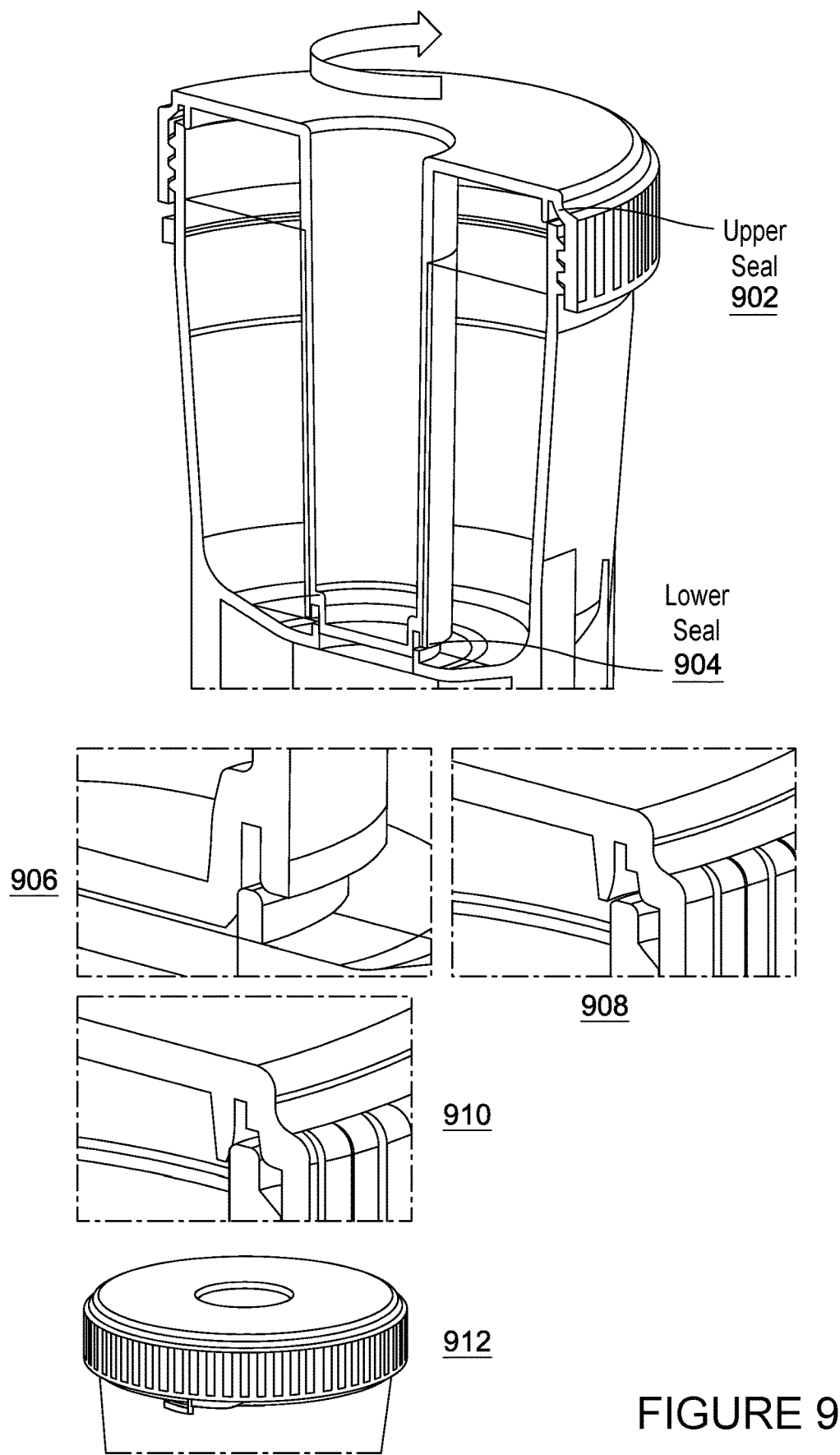
FIG. 9 shows a cap seal design for a sample collection container, according to some embodiments.
Figure 10:
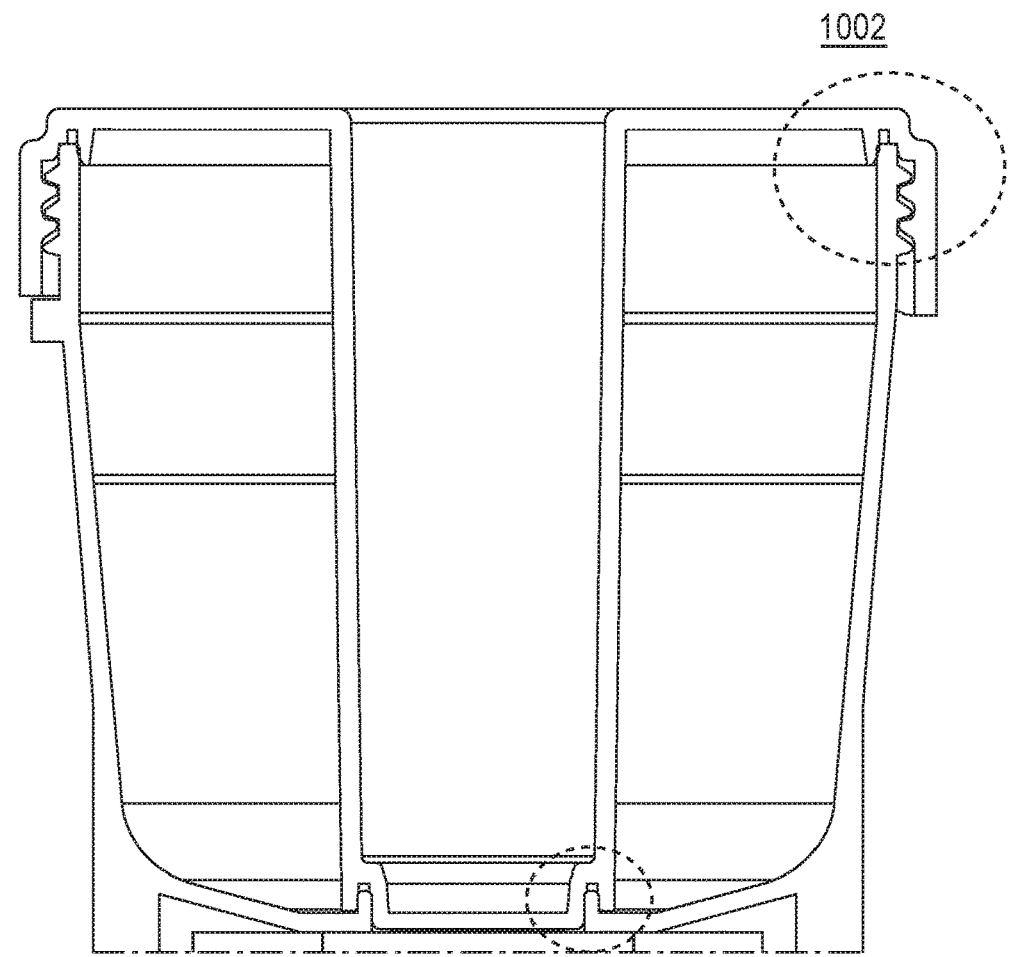
FIG. 10 shows a cap seal design for a sample collection container, according to some embodiments.
Figure 10:
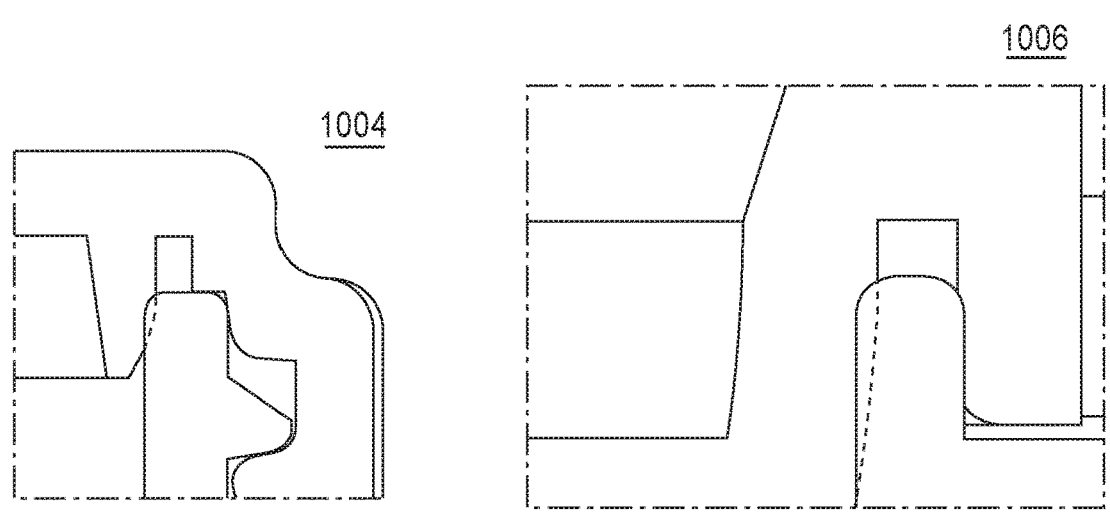
Figure 11:
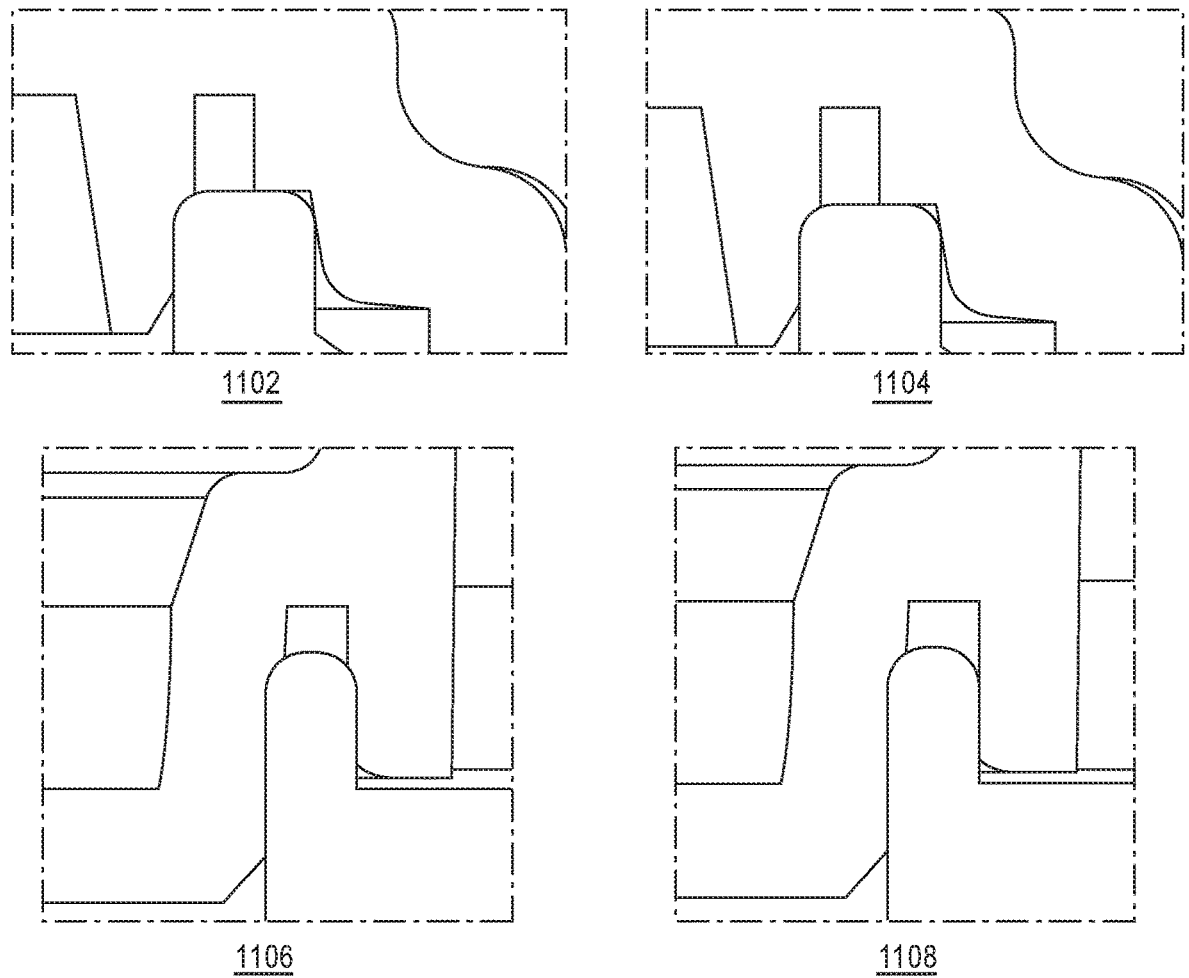
FIG. 11 shows a cap seal design for a sample collection container, according to some embodiments.

FIG. 9 shows a top cap seal design for a sample collection container, according to some embodiments. For example, the top cap may comprise a lower seal 904 which may seal the lower volume chamber from the upper volume chamber. In some embodiments, the bottom seal may start engagement with the sealing rib of the first volume 906 before the top seal has been engaged 908. In some embodiments, this may start at 0.06 inches from the end of the travel. The top seal 902 may seal the top of the sample collection container, and may start to engage at the end of the travel at the top of the container 910, e.g., at 0.03 inches from the end of the travel, and/or the like. The cap may be rotated along the thread of the container until the cap stop on the top cap connects with a clasp 912 on the container, preventing further rotation and securing the top cap in place. In some embodiments, the lower and upper volumes of the sample may be pressurized to exemplary pressures of 0.82 PSIG and 1.1 PSIG, respectively, when the top cap is fully closed on the container. Referring to FIG. 10, the top cap may fit snugly along the thread of the top portion of the container 1002. The top seal may have a nominal interference of approximately 0.008 inches 1004, and the bottom seal may have a nominal interference of 0.010 inches 1006. Referring to FIG. 11, the top seal may vary in its thickness due to interference by the container, e.g., by a factor of +/−0.003 inches, or may vary in depth, e.g., by a factor of +/−0.020 inches. Thus, for example, the thickness of the top seal could be 0.003 inches and the depth 0.011 inches 1102 or the thickness could be −0.003 inches with a depth of 0.005 inches 1104. In some embodiments, 0.014 inches of interference may be greater than nominal, and 0.002 inches of interference may be below nominal. Similarly, the bottom seal may also vary in thickness due to interference, e.g., by a factor of +/−0.003 inches, or may vary in depth, e.g., by a factor of +/−0.020 inches. Thus, the thickness of the bottom seal could be 0.005 inches with a depth of 0.011 inches 1106 or could have a thickness of −0.001 inches with a depth of 0.003 inches 1108.

Figure 12:
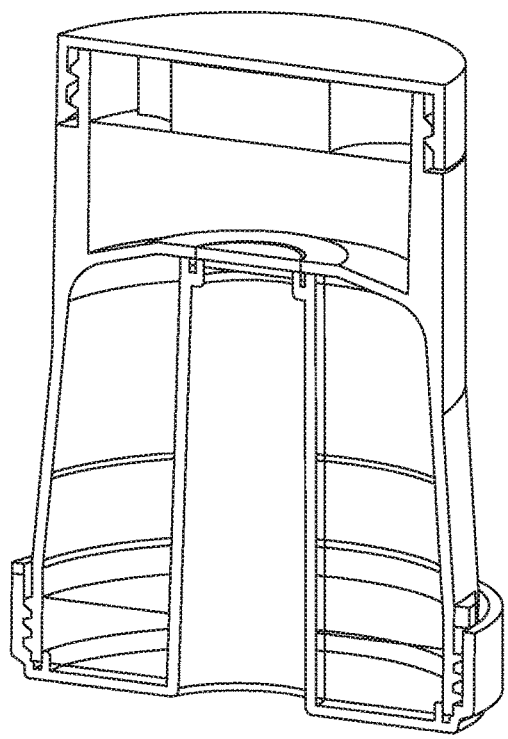
FIG. 12 shows extracting samples from a sample collection container, according to some embodiments.
Figure 12:
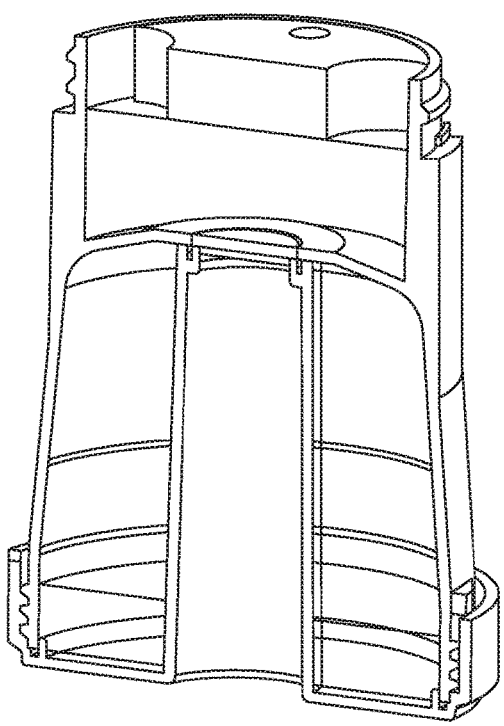
Figure 12:
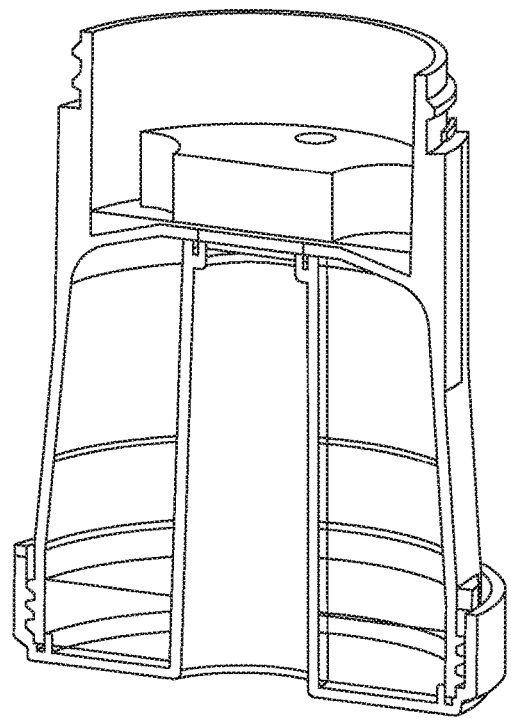
Figure 13:
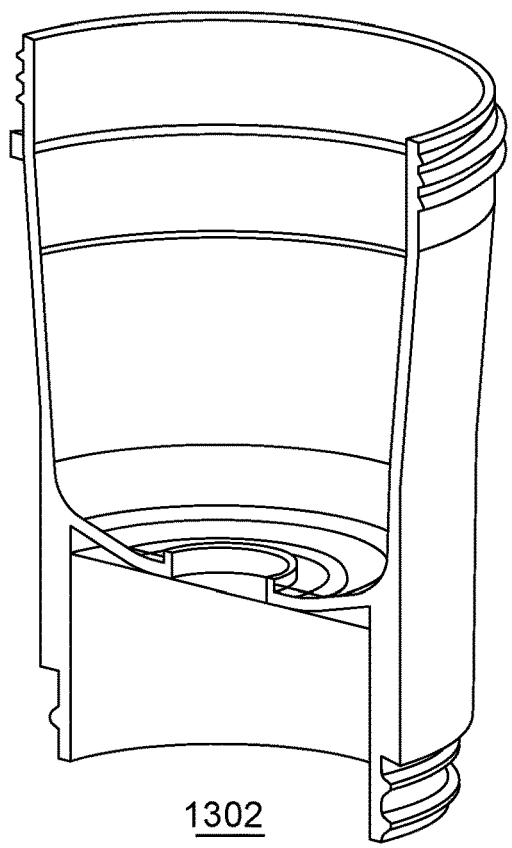
FIG. 13 shows volume areas in a sample collection container, according to some embodiments.
Figure 13:
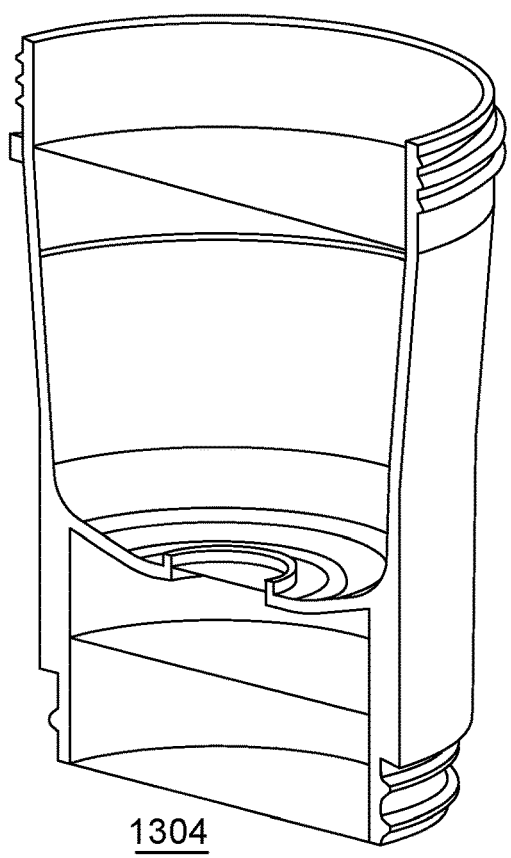

FIG. 12 shows extracting samples from a sample collection container, according to some embodiments. The container may be inverted 1202 such that the bottom cap is facing upward, and the bottom cap may be removed from the container. The sample in the lower volume chamber may be removed 1204, e.g., using the fluid access cutouts and/or pass-through holes in the float. As more of the sample is removed, the float may move to the bottom of the chamber 1206. Referring to FIG. 13, the container may have dead volume areas in both the top and bottom chambers of the container 1302, e.g., of 0.77 mL below the sealing rim in the upper volume, and of 1.72 mL at the top of the lower volume. The upper and lower volumes may contain 95 mL and 25 mL of sample, respectively 1304.

Figure 14:
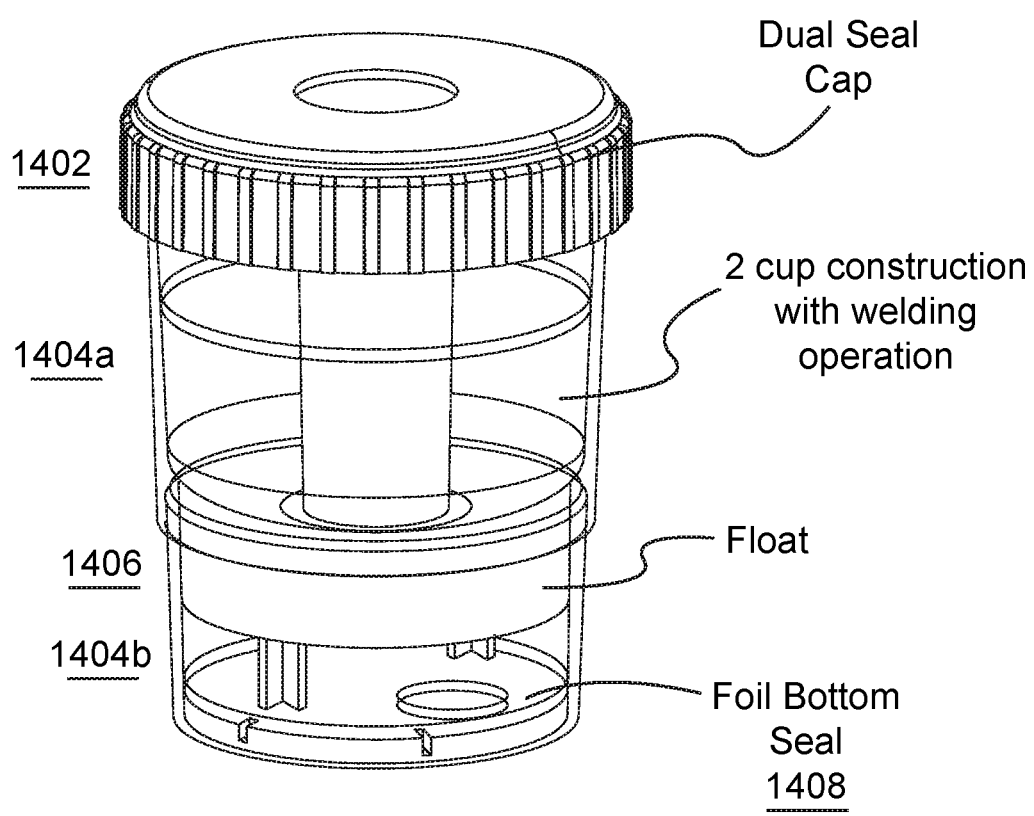
FIG. 14 shows a two-cup design for a sample collection container, according to some embodiments.
Figure 15:
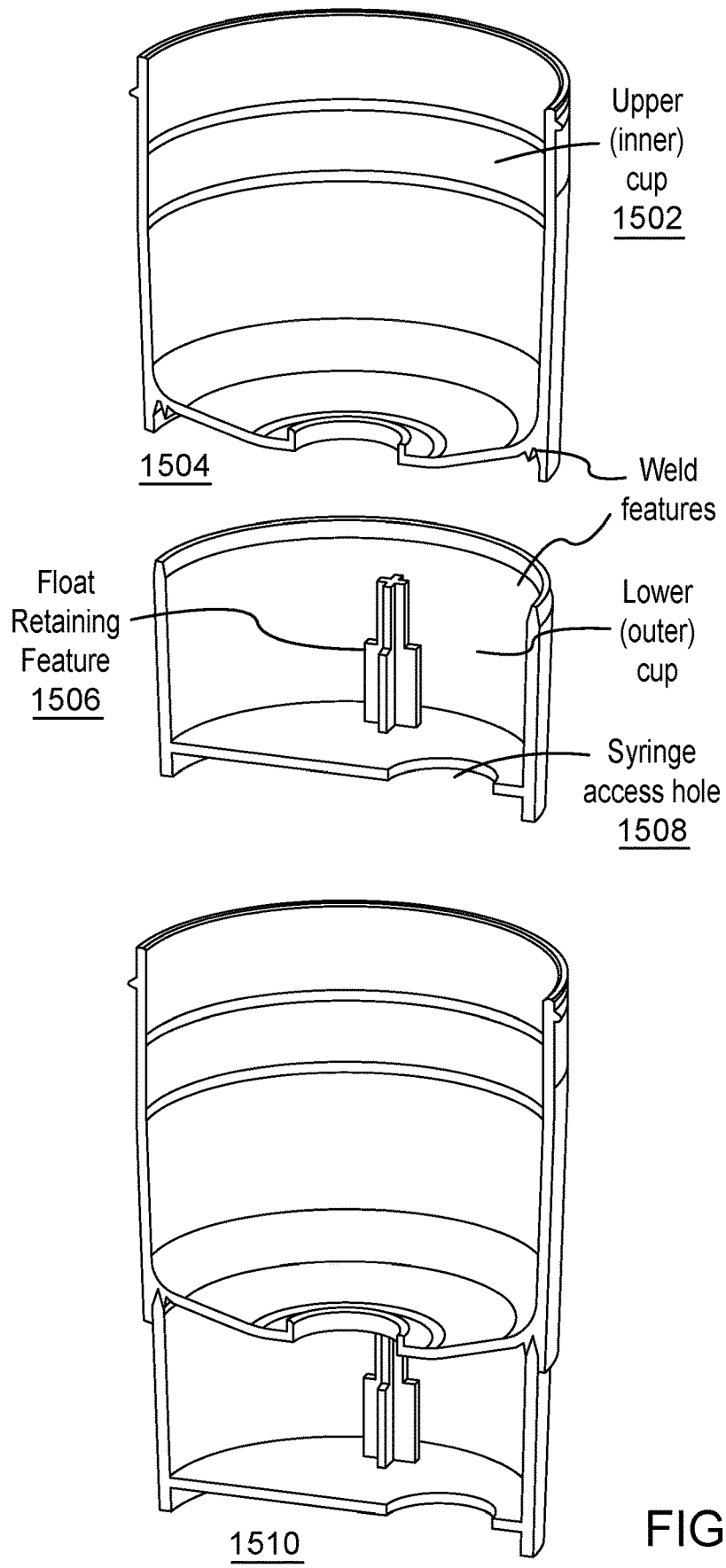
FIG. 15 shows a two-cap design for a sample collection container, according to some embodiments.
Figure 16:
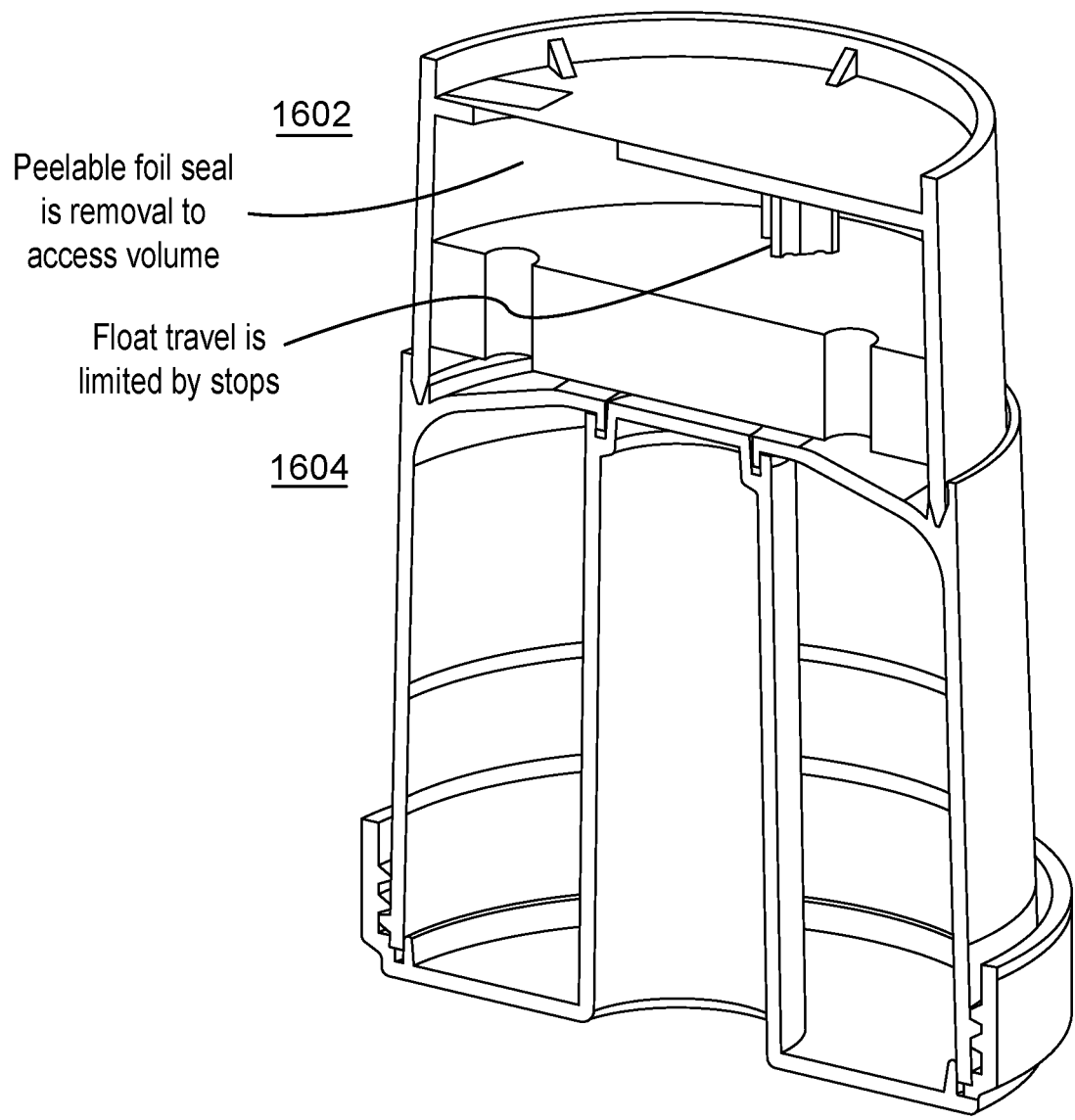
FIG. 16 shows an assembled two-cap design for a sample collection container, according to some embodiments.
Figure 17:
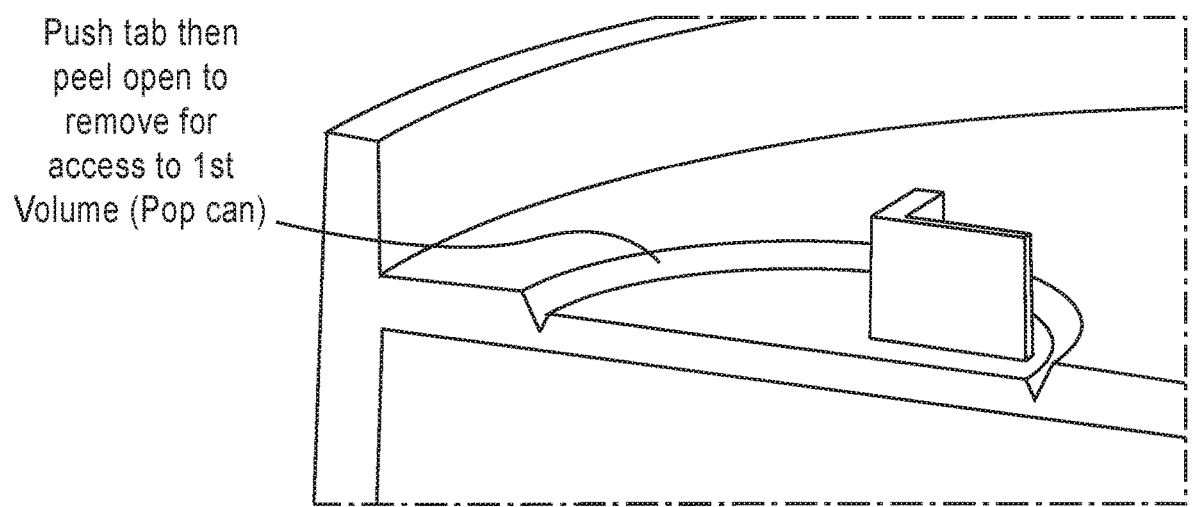
FIG. 17 shows a seal design for a sample collection container, according to some embodiments.

FIG. 14 shows a two-cup design for a sample collection container, according to some embodiments. A two-cup design may include an upper (e.g., inner) collection cup container 1404a and a lower (e.g., outer) collection cup container 1404b, with no bottom cap. In some embodiments, the a two-cup design for a collection container may have a diameter of 2.6 inches and a height of 3.3 inches, and/or like dimensions. The top of the container may be closed with a dual-seal cap 1402, and a float device 1406 in the lower collection cup container. In some embodiments, a seal 1408 may be used for sealing a syringe access hole in the lower collection cup. The seal may be foil, plastic, and/or a plurality of other materials. In some embodiments the outer surface of the collection container may not comprise any ribs, and may be smooth. Referring to FIG. 15, the upper collection cup container 1502 may be detachable from the lower collection cup container 1508, and may have weld features 1504 which allow for the two cups to fit on top of each other. The lower collection cup may also have a float retaining mechanism 1506 designed to limit the movement of a float in the lower collection cup. In some embodiments, the two cups may stack on top of each other 1510 and may lock into place in order to secure the cups together. The collection container components may be made of food grade polypropylene, and may have a thickness of approximately 0.06 inches. Referring to FIG. 16, the seal 1602 may be peelable from the bottom of the lower collection cup, e.g., in order to access the volume of the sample contained in the lower collection cup. The float 1604 may be able to move in the lower collection cup based on the volume of the sample contained in the lower collection cup, and/or may also have its movement limited by a float stop and/or retaining mechanism. Referring to FIG. 17, in some embodiments, the seal may comprise a push tab 1702 that the user may use to open and peel the seal from the lower collection cup.

Figure 18:
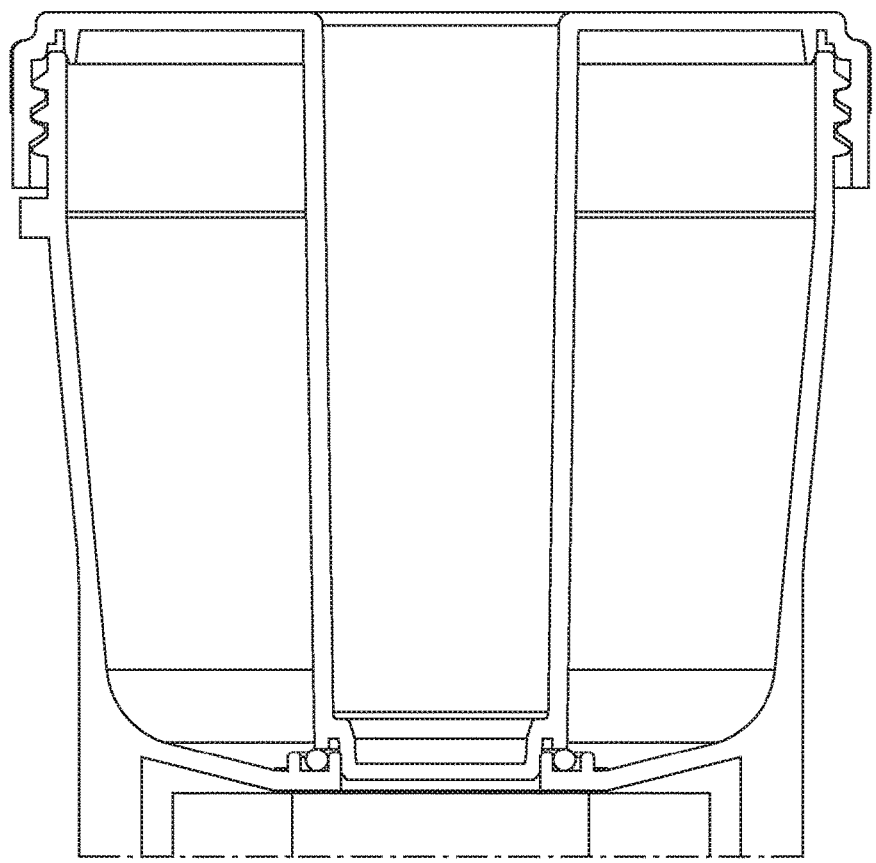
FIG. 18 shows a cap seal design for a sample collection container, according to some embodiments.
Figure 18:
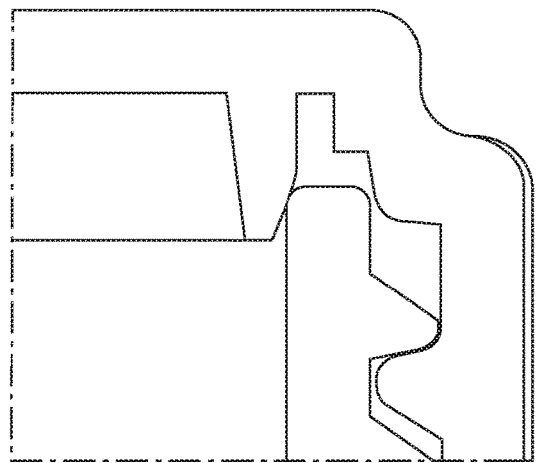
Figure 18:
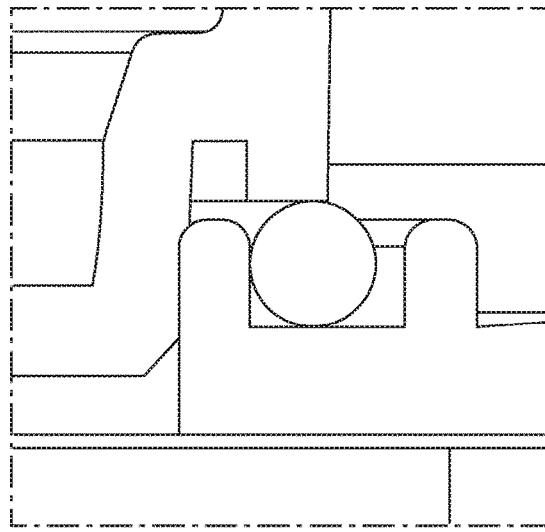
Figure 19:
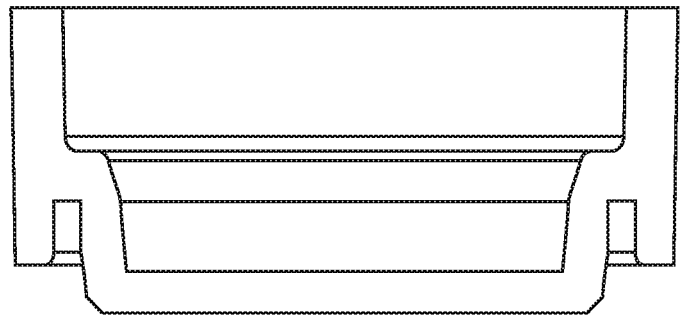
FIG. 19 shows seal area thickness for a sample collection container, according to some embodiments.
Figure 19:
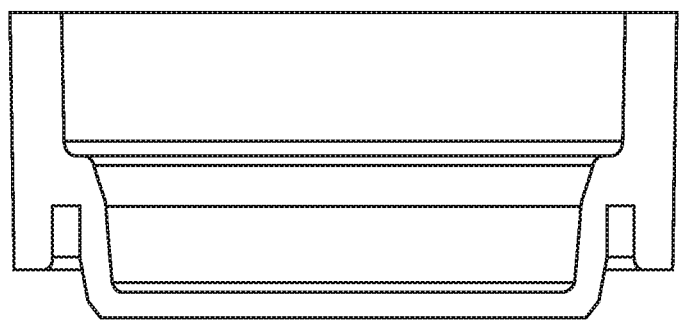

FIG. 18 shows a cap seal design for a sample collection container, according to some embodiments. In some embodiments, the top cap 1802 may comprise both a screw cap component and a protrusion from the screw cap component which may seal off a hole between the upper collection cup and the lower collection cup. The screw cap may comprise a top seal 1804 which may seal the top of the sample collection container, and a bottom seal 1806 which may seal the upper collection cup from the lower collection cup (e.g., to prevent dilution of the sample in the lower collection cup, and/or the like), e.g., by fitting together with an inner and outer boss surrounding a gap area between the upper collection cup and the lower collection cup. The bottom seal may comprise a rubber seal (e.g., an O-ring and/or like device which may grip the ID of the boss of the upper collection cup). and/or stopper in order to help strengthen the seal between the collection cups. Referring to FIG. 19, the bottom seal may be formed such that there is either a 0.001 inch deflection at 20 pounds 1902, or an 0.003 inch deflection at 20 pounds 1904, e.g., depending on the thickness of the protrusion affecting the bottom seal, and/or the like.

Figure 20:
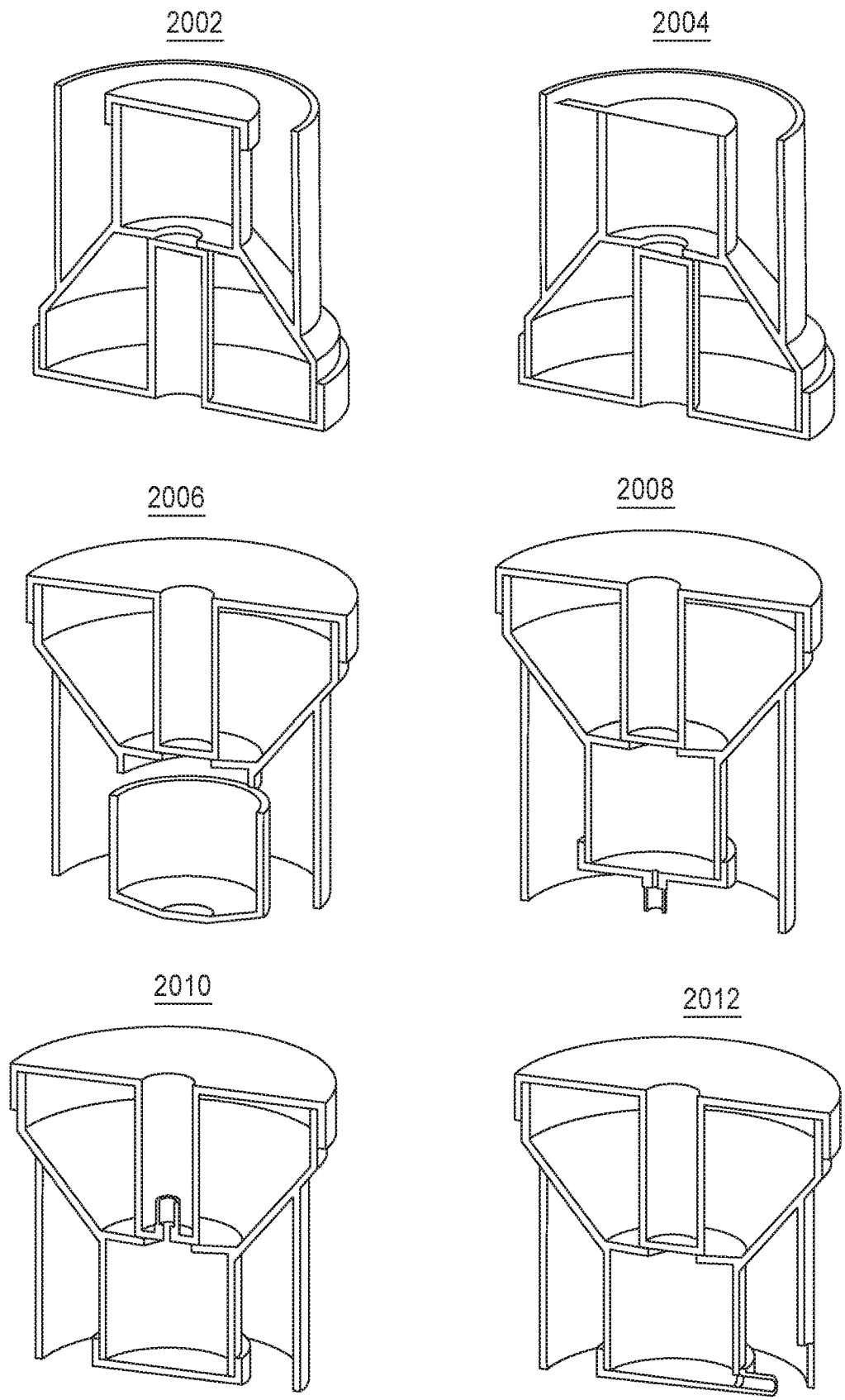
FIG. 20 shows designs for a sample collection container, according to some embodiments.

FIG. 20 shows designs for a sample collection container, according to some embodiments. For example, a sample collection container may comprise a single container with a cap on the bottom of the container 2002, a single container with a seal (e.g., a foil seal, and/or the like) which can be peeled off and/or punctured 2004, a container with a removeable cup on the bottom of the container 2006, and/or a container with a luer (e.g., a luer on the bottom of a bottom cap 2008, a luer on the bottom of the protrusion sealing off the lower volume of the collection container from the upper volume 2010, a luer on the side of a bottom cap 2012, and/or the like).

Any and all references to publications or other documents, including but not limited to, patents, patent applications, articles, webpages, books, etc., presented in the present application, are herein incorporated by reference in their entirety, except insofar as the subject matter may conflict with that of the embodiments of the present disclosure (in which case what is present herein shall prevail). The referenced items are provided solely for their disclosure prior to the filing date of the present application. Nothing herein is to be construed as an admission that any invention disclosed herein is not entitled to antedate such material by virtue of prior invention.

Although example embodiments of the apparatuses, methods and systems have been described herein, other modifications to such embodiments are possible. These embodiments have been described for illustrative purposes only and are not limiting. Other embodiments are possible and are covered by the disclosure, which will be apparent from the teachings contained herein. Thus, the breadth and scope of the disclosure should not be limited by any of the above-described embodiments but should be defined only in accordance with claims supported by the present disclosure and their equivalents. In addition, any logic flow depicted in the above disclosure and/or accompanying figures may not require the particular order shown, or sequential order, to achieve desirable results. Moreover, embodiments of the subject disclosure may include methods, systems and devices which may further include any and all elements from any other disclosed methods, systems, and devices, including any and all elements corresponding to the collection of biological fluids. In other words, elements from one and/or another disclosed embodiment may be interchangeable with elements from other disclosed embodiments. In addition, one or more features/elements of disclosed embodiments may be removed and still result in patentable subject matter (and thus, resulting in yet more embodiments of the subject disclosure). Still further, some embodiments of the present disclosure may be distinguishable from the prior art for expressly not requiring one and/or another feature disclosed in the prior art (e.g., some embodiments may include negative limitations). Some of the embodiments disclosed herein are within the scope of at least some of the following exemplary claims of the numerous claims which are supported by the present disclosure which may be presented.

What is currently claimed is:

1. A sample collection container apparatus, comprising:
   a top end;
   a bottom end arranged opposite and parallel to the top end;
   a first volume area of a sample collection container, wherein the first volume area is configured to contain a first volume of a sample;
   a second volume area of the sample collection container, wherein the second volume area is configured to contain a second volume of the sample after the first volume area of the sample collection container has been filled;
   an opening between a first end of the first volume area and a first end of the second volume area;

a top cap arranged on the top end and removable from a second end of the second volume area and having a seal configured to seal the opening between the first and second volume areas upon the top cap being affixed to the second end of the second volume area of the sample collection container;

a bottom cap arranged on the bottom end and removable from a second end of the first volume area of the sample collection container so as to allow extraction of the first volume of the sample from the first volume area of the sample collection container upon the sample collection container being placed in a second position; and a float device arranged within the first volume area of the sample collection container, the float device including:
 a top surface and a bottom surface,
 at least one open fluid access cutout passing from the top surface to the bottom surface, and
 a section integral with the top surface and configured to block the opening between the first volume area and the second volume area when the apparatus is in the first position, wherein:
 the float device is configured to allow a sample extraction device to access the first volume of the sample through the at least one open fluid access cutout upon the apparatus being in the second position, and
 upon the sample collection container being arranged in a first position, opposite to the second position, and the top cap removed, so as to receive the sample from the second end of the second volume area, the float device is configured to:
  float in a first direction toward the opening as the first volume area is filled with the sample received from the second volume area through the opening, and
  seal the first volume area from the second volume area upon the float having reached the opening after receiving the first volume of the sample.

2. The apparatus of claim 1, wherein the first volume of the sample is a first portion of the sample.

3. The apparatus of claim 2, wherein the first portion of the sample is the first 25 ml of the sample.

4. The apparatus of claim 1, wherein the sample extraction device is a syringe.

* * * * *